(12) United States Patent
Alcarazo et al.

(10) Patent No.: US 8,981,126 B2
(45) Date of Patent: Mar. 17, 2015

(54) CYCLOPROPENYLIDENE-STABILIZED PHOSPHENIUM CATIONS

(75) Inventors: Manuel Alcarazo, Mülheim an der Ruhr (DE); Hans Bruns, Duisburg (DE); Jekaterina Petuskova, Riga (LV)

(73) Assignee: Studiengesellshaft Kohle mbH, Muelheim an der Ruhr (DE)

( * ) Notice: Subject to any disclaimer, the term of this patent is extended or adjusted under 35 U.S.C. 154(b) by 0 days.

(21) Appl. No.: 14/000,997

(22) PCT Filed: Feb. 23, 2012

(86) PCT No.: PCT/DE2012/100046
§ 371 (c)(1),
(2), (4) Date: Sep. 23, 2013

(87) PCT Pub. No.: WO2012/113393
PCT Pub. Date: Aug. 30, 2012

(65) Prior Publication Data
US 2014/0051870 A1    Feb. 20, 2014

(30) Foreign Application Priority Data
Feb. 24, 2011  (DE) .......................... 10 2011 012 334

(51) Int. Cl.
| C07D 311/94 | (2006.01) |
| C07F 9/50 | (2006.01) |
| B01J 31/24 | (2006.01) |
| C07F 15/00 | (2006.01) |
| C07F 1/12 | (2006.01) |

(52) U.S. Cl.
CPC ............ *C07F 9/5018* (2013.01); *C07F 9/5022* (2013.01); *C07F 15/0073* (2013.01); *C07F 15/0093* (2013.01); *C07F 1/12* (2013.01); *B01J 31/2404* (2013.01); *C07D 311/94* (2013.01)
USPC .................. 549/388; 564/15; 556/19; 556/13

(58) Field of Classification Search
USPC ........................... 549/388; 564/15; 556/19, 13
See application file for complete search history.

(56) References Cited

FOREIGN PATENT DOCUMENTS

JP           51070756 A   *  6/1976  ................ C07F 9/54

OTHER PUBLICATIONS

Petuskova et al., Cyclopropenylylidene-Stabilized Diaryl and Dialkyl Phosphenium Cations: Applications in Homogeneous Gold Catalysis, 2011, Angew. Chem. Int. Ed., 50, 3799-3802.*
Huy et al, "The Phosphorus Versiion of the Oxaspiropentene—Cyclobutenone Rearrangement"; Organometallics, vol. 29, No. 5, Mar. 8, 2010, pp. 1302-1304.
Landau et al, "Pseudooxokohlenstoff-Anionen der Seimdreiecksäure"; Chem. Ber., vol. 124, No. 3, 1991, pp. 665-669.
English translation of the International Search Report of corresponding PCT/DE2012/100046 mailed Aug. 28, 2012.

* cited by examiner

*Primary Examiner* — Kristin Vajda
(74) *Attorney, Agent, or Firm* — Norris McLaughlin & Marcus, P.A.

(57) ABSTRACT

Phosphenium compounds with the general formula I:

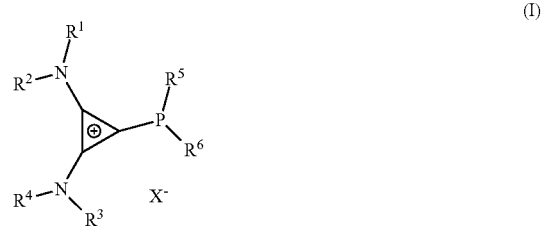

(I)

in which $R^1$, $R^2$, $R^3$ and $R^4$ are identical or different and represent a linear or branched $C_1$-$C_6$-alkyl radical, which can optionally be substituted, or $R^1$ and $R^2$ and/or $R^3$ and $R^4$ are bonded to one another with the formation of a ring, $R^5$ and $R^6$ stand for a saturated or unsaturated and linear or branched alkyl group, alkenyl group or aryl group, which can have suitable substituents, even heteroatoms as substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, $X^-$ represents an anion, a process for the preparation thereof, and also the use of these compounds in metal complexes which can be used as catalysts in organic synthesis, are claimed.

12 Claims, No Drawings

CYCLOPROPENYLIDENE-STABILIZED PHOSPHENIUM CATIONS

This application is a 371 of International Patent Application No. PCT/DE2012/100046 filed Feb. 23, 2012, which claims foreign priority benefit under 35 U.S.C. §119 of the German Patent Application No. 10 2011 012 334.2, filed Feb. 24, 2011, the disclosures of which are incorporated herein by reference.

The present invention relates to novel stabilized cyclopropenylylidene cations and their use as ligands in metal catalysts.

Phosphenium cations of the general formula $[R_2P:]^+$ are isolobal with singlet carbenes and can be stabilized, for example, by donation of electron density in their empty orbital. This stabilization can, for example, be achieved by incorporation of the phosphorus atom in a heterocyclic backbone A or by reaction with bases with the formation of the corresponding Lewis adduct B (scheme 1).

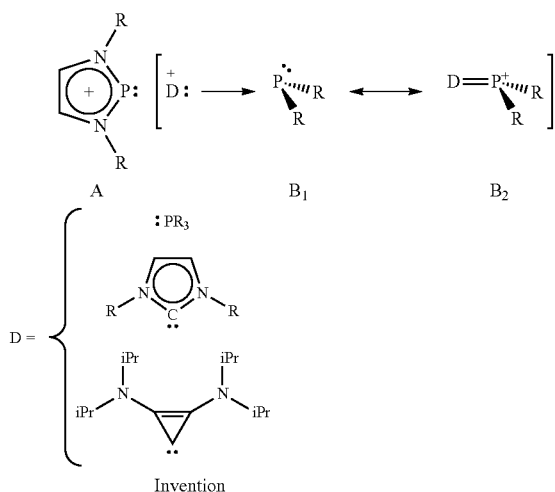

In both cases, the presence of a free electron pair on the phosphorus atom suggests the use of these compounds as ligands, though their intrinsic positive charge results in them being weak σ donors and strong π acceptors. In particular, in the adducts of type B, the resonance structure of $B_2$ dominates in the basic structure, if D is a phosphine, so that transition metal complexes, which can be derived from these compounds, are rare. Even in cases in which D is an N-heterocyclic carbene (NHC), the coordination properties of the resulting adducts are simply comparable with those which show strong π acceptor phosphites.

It is an object of the present invention to make available compounds in which the phosphenium structure is stabilized and which can be used as ligands in noble metal complexes.

The subject matter of the present invention are phosphenium compounds with the general formula I

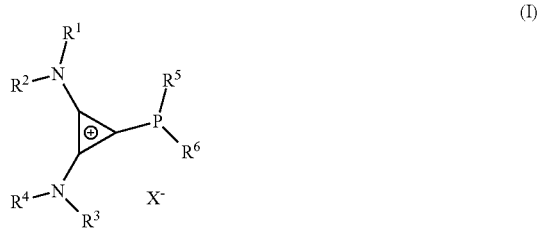

(I)

in which $R^1$, $R^2$, $R^3$ and $R^4$ are identical or different and represent a linear or branched $C_1$-$C_6$-alkyl radical, which can optionally be substituted, or $R^1$ and $R^2$ and/or $R^3$ and $R^4$ are bonded to one another with the formation of a ring, $R^5$ and $R^6$ stand for a saturated or unsaturated and a linear, branched or cyclic alkyl group, alkenyl group or aryl group, which can have suitable substituents, even heteroatoms as substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, $X^-$ represents an anion.

Surprisingly, it has been determined that the phosphenium compounds according to the invention which are stabilized with cyclopropenylylidene can be obtained in good yields by condensation of the readily available chlorocyclopropenium salt with secondary phosphines and subsequent anion exchange. In some cases, an anion exchange is carried out in order if appropriate to replace anions resulting from the preparation process by the appropriate desired anion. This is in particular then necessary if Cl anions are present, which can have a disadvantageous affect on the catalytic activity.

The compounds are obtained as white air-stable solids.

The compounds according to formula I are "phosphenium" compounds. These compounds can be represented in two limiting structures:

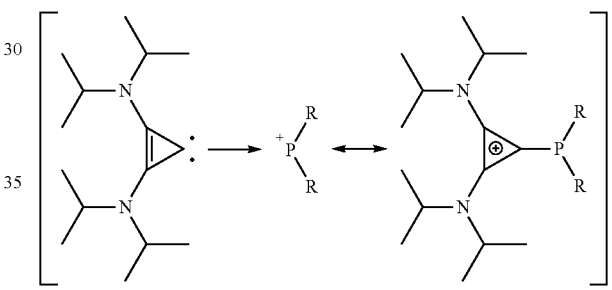

The Inventors have determined that the stabilization of the cations takes place via the amino radicals on the cyclopropenium radical. Particularly stable compounds are obtained if $R^1$, $R^2$, $R^3$ and $R^4$, each independently of one another, are chosen from isopropyl and tert-butyl. Particularly preferably, $R^1$, $R^2$, $R^3$ and $R^4$ each have the same meaning. Particularly readily available are compounds in which these radicals represent isopropyl.

The anion $X^-$ can be any suitable anion which does not affect the stability of the cation and also makes possible the reaction of the compounds according to the invention to give transition metal complexes. Examples of suitable anions are $BE_4^-$, $PF_6^-$, $SbF_6^-$ and/or $BPh_4^-$.

The radicals $R^1$, $R^2$, $R^3$ and $R^4$ used in the context of the present invention are preferably a linear or branched $C_1$-$C_6$-alkyl radical. The radicals $R^5$ and $R^6$ are preferably chosen from linear or branched or cyclic alkyl radicals, aryl radicals or alkylaryl radicals. $R^5$ and $R^6$ preferably represent optionally substituted phenyl radicals, such as $C_1$-$C_4$-alkylphenyl, $C_1$-$C_4$-alkoxyphenyl or halophenyl, or cyclic alkanes, such as cyclohexyl or adamantyl.

Insofar as the term "hydrocarbon group" is used, it means, in the context of the invention, a saturated or unsaturated and linear or branched alkyl group, alkenyl group, aryl group or alkylaryl group, which can have suitable substituents, even heteroatom substituents, or a heteroatom-comprising hydrocarbon group.

Alkyl can be unbranched (linear) or branched and have from 1 to 6 carbon atoms. Alkyl is preferably methyl, ethyl, propyl, isopropyl, butyl, isobutyl, sec-butyl or tert-butyl, as well as pentyl, 1-methylpropyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, or 1,1,2- or 1,2,2-trimethylpropyl. Alkyl can also represent halogenated alkyl radicals, e.g. trifluoromethyl, pentafluoroethyl or 1,1,1-trifluoroethyl.

Cycloalkyl is preferably cyclopropyl, cyclobutyl, cyclopentyl, cyclohexyl or cycloheptyl but can also mean adamantyl.

Alkylene preferably means methylene, ethylene, propylene, butylene, pentylene or hexylene but also branched alkylene.

Aryl is preferably phenyl, naphthyl or diphenyl and arylalkyl is preferably benzyl.

Examples of substituents are $C_1$-$C_4$-alkyl, such as methyl, ethyl, propyl, isopropyl, butyl, isobutyl, sec-butyl or tert-butyl, $C_1$-$C_4$-alkenyl, preferably vinyl or propenyl, $C_1$-$C_4$-alkoxy, such as methoxy, ethoxy, propoxy or butoxy, aryl, heteroaryl, halogen, such as F, Cl, Br, or I, $NO_2$, $NH_2$, and the like.

The compounds according to the invention with the formula I can be obtained by reaction of the halocyclopropenium salts with phosphines. An additional subject matter of the present invention is accordingly a process for the preparation of phosphenium compounds with the general formula I

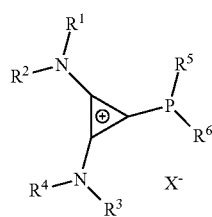

(I)

in which $R^1$, $R^2$, $R^3$, $R^4$, $R^5$, $R^6$ and $X^-$ are defined as above, in which halocyclopropenium salts with the general formula II

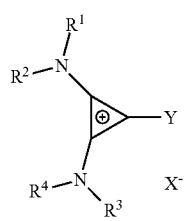

(II)

in which $R^1$, $R^2$, $R^3$, $R^4$ and $X^-$ are defined as above and Y represents a halogen atom, are reacted with a phosphine of the general formula III $HPR^5R^6$ (III)

in which $R^5$ and $R^6$ are defined as above.

The preparation of the compounds according to the invention with the formula I can be carried out in a simple way known to the person skilled in the art. In one possible embodiment of the preparation process, the starting compounds are dissolved in a suitable solvent and reacted with one another over a sufficient period of time, optionally at elevated temperature, up to the boiling temperature of the solvent. The reaction product obtained can be used further without additional treatment. The starting compounds react virtually quantitatively with one another. In treating the product, it may in some cases be necessary to wash the product with a suitable solvent. Additional purification steps are not usually necessary. For the case in which damaging anions are present, the product, for the treatment thereof, can be washed with a saturated solution comprising the desired anions, in order thus to bring about anion exchange.

Use is preferably made, as starting compounds with the formula II, of those compounds in which Y represents Cl.

The compounds with the formula I can be isolated in good yields from the reaction mixture.

The reaction of the starting compounds for the preparation of the compounds according to the invention with the formula I is preferably carried out in a solvent. Use may be made, as solvent, of all normal polar or nonpolar organic solvents, for example $CH_2Cl_2$, $ClCH_2CH_2Cl$, toluene, THF, dimethoxyethane (DME), dimethylformamide (DMF), dimethyl sulfoxide (DMSO), N-methyl-2-pyrrolidone (NMP) or 1,4-dioxane and any mixtures thereof.

The compounds according to the invention with the formula I can be used as ligands for transition metal complexes. They are particularly suitable as ligands for metal complexes.

An additional subject matter of the present invention is accordingly the use of the compounds with the formula I as ligands in metal complexes, in particular in metal catalysts.

Yet a further subject matter of the present invention are metal complexes with the formula IV,

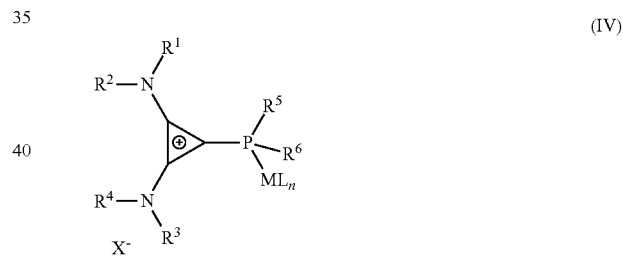

(IV)

in which $R^1$, $R^2$, $R^3$, $R^4$, $R^5$, $R^6$ and $X^-$ are defined as in claim 1, M stands for a metal ion chosen from the group consisting of B, Cu, Ag, Au, Ru, Rh, Pd, Os, Ir and Pt, L represents n identical or different ligands and n represents a number from 1 to 3, and the use of these metal complexes as catalysts.

The metal complexes according to the invention can exhibit both one or more ligands L and one or more compounds with the formula I as additional ligands, as well as one or more metal centers. The ligands L can be identical or different and can be chosen from compounds of the formula I or normal ligands, such as are known for metal complex compounds, e.g. halogen (such as F, Cl, Br or I), CN, CO or mono- and polyunsaturated organic radicals, inclusive of ring systems, such as alkenes, cycloalkenes or alkynes, e.g. cyclopentene, cyclopentadiene, cyclohexene, cyclohexadiene, cyclooctene, cyclooctadiene and/or allyl.

For the preparation of these metal complexes, the compounds with the formula I can be reacted with the corresponding metal compounds $ML_n$. The reaction usually takes place quantitatively. The reaction of the compounds with the formula I with the metal compounds is preferably carried out in solutions. The abovementioned solvents are suitable as solvents.

The metal compounds $ML_n$ used for the preparation of the metal complexes can be any metal compounds, such as metal salts and/or metal complexes, of the metals B, Cu, Ag, Au, Ru, Rh, Pd, Os, Ir and Pt. Preferably, compounds used are chosen from AuCl, AuCl$_3$, PdCl(allyl), RhCl(cod), RhCl(CO)$_2$, CuCl, RhC14 and BH$_3$.

The metal complexes are suitable as catalysts in organic synthesis; for example, they can be used in cycloisomerizations.

Examples of such reactions are represented below.

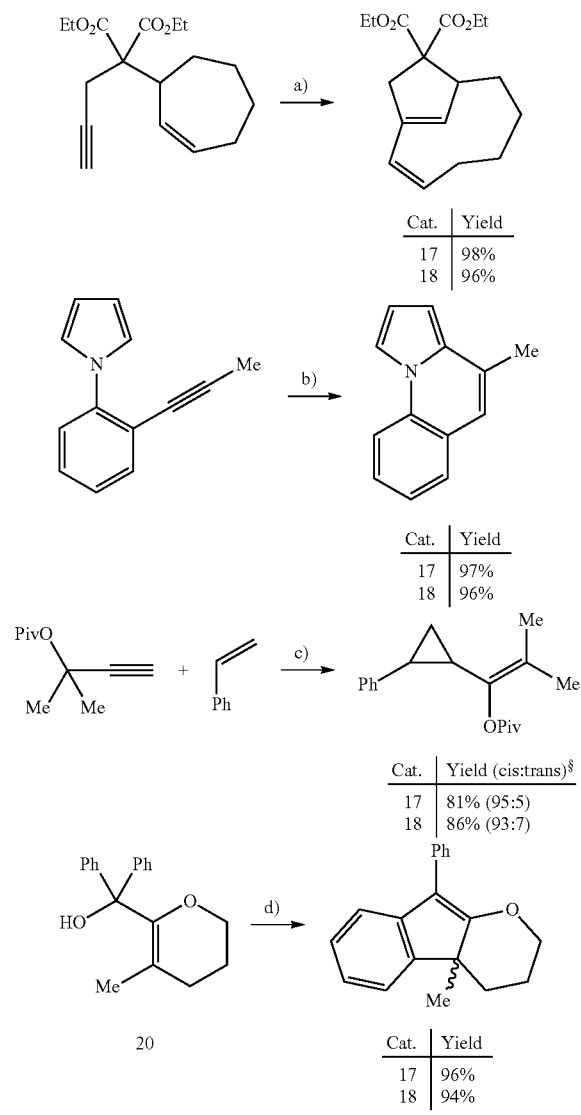

EXAMPLES

All reactions were carried out in dried glass flasks under an Ar atmosphere. The solvents were purified by distillation over a dehydrating agent and likewise stored under argon: THF, Et$_2$O (Mg-anthracene), CH$_2$Cl$_2$ (CaH$_2$), MeCN, Et$_3$N (CaH$_2$), MeOH (Mg), hexane or toluene (Na/K). Lesch chromatography: Merck Silica gel 60 (230-400 mesh), IR: Nicolet FT 7199 spectrometer, wavenumbers in cm$^{-1}$, MS(EI): Finnigan MAT 8200 (70 eV), LSIMS: Finnigan MAT 95, mass determinations: Bruker Apex III FT-MS (7T magnet), NMR: spectra were recorded in the specified solvents on a Bruker DPS 300 or AV 400 spectrometer, $^1$H and $^{13}$C shift (δ are indicated in ppm relative to TMS, coupling constants J) in Hz. The solvent signals were used as references and the shifts converted to the TMS scale. Melting points: Büchi melting point determination apparatus B-540 (corrected). Element analyses: H. Kolbe, Mülheim/Ruhr. All commercially available compounds were used without additional treatment, unless otherwise indicated. 2,3-Bis(diisopropylamino)-1-chlorocyclopropenium tetrafluoroborate 1 was prepared according to the literature method (R. Weiss, K. G. Wagner, C. Priesner and J. Macheleid, *J. Am. Chem. Soc.*, 1985, 107, 4491-4499).

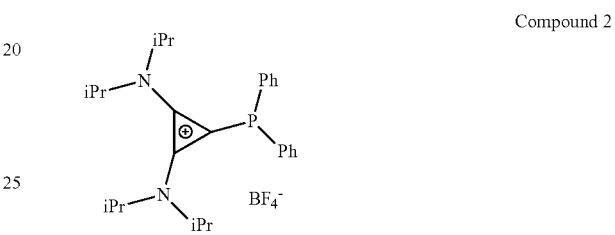

Compound 2

Diphenylphosphine (2.9 ml, 16.7 mmol) was added to a mixture of chlorocyclopropenium salt 1 (2.0 g, 5.58 mmol) in THF (20 ml) and the mixture obtained was heated at 60° C. for 24 hours. After cooling to ambient temperature, the solvent was removed under vacuum and the residue was dissolved in DCM (30 ml), washed with a saturated NaBF$_4$ solution (3×25 ml) and dried over Na$_2$SO$_4$. The organic phase was evaporated and the residue was washed with Et$_2$O (3×10 ml). The compound was obtained as a white solid (2.55 g, 90%).

$^1$H NMR (300 MHz, CD$_2$Cl$_2$) δ=0.98 (d, J=6.8 Hz, 12H), 1.29 (d, J=6.8 Hz, 12H), 3.34 (sep, J=6.8 Hz, 2H), 3.99 (sep, J=6.8 Hz, 2H), 7.32-7.47 ppm (m, 10H). $^{31}$P NMR (121 MHz, CD$_2$Cl$_2$) δ=−23.61 ppm. $^{13}$C NMR (75 MHz, CD$_2$Cl$_2$) δ=21.6, 22.0, 53.6, 107.1 (d, J=66.8 Hz), 130.5 (d, J=8.1 Hz), 131.4 (d, J=8.1 Hz), 131.7, 134.7 (d, J=21.2 Hz), 139.7 ppm. IR (neat) ν=695, 752, 1047, 1547, 1867, 2974 cm$^{-1}$. HRMS calculated for C$_{27}$H$_{38}$N$_2$P$^+$: 421.276711. found 421.276467.

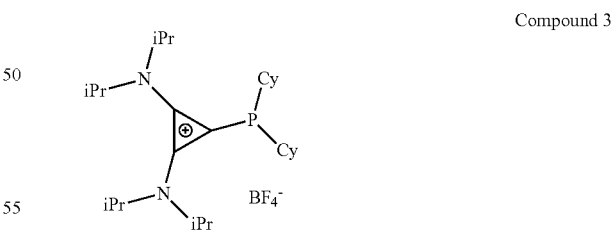

Compound 3

Dicyclohexylphosphine (0.84 ml, 4.17 mmol) was added to a mixture of chlorocyclopropenium salt 1 (500 mg, 1.39 mmol) in THF (5 ml) and the mixture obtained was heated at 60° C. for 24 hours. After cooling to ambient temperature, the solvent was removed under vacuum and the residue was dissolved in DCM (20 ml), washed with saturated NaBF$_4$ solution (3×15 ml) and dried over Na$_2$SO$_4$. The organic phase was evaporated and the residue was washed with Et$_2$O (3×5 ml) and gave the desired compound as a white solid (620 mg, 86%).

¹H NMR (300 MHz, CD₂Cl₂) δ=0.96-1.24 (m, 8H), 1.31 (d, J=6.6 Hz, 12H), 1.33 (d, J=6.8 Hz, 12H), 1.35-1.51 (m, 6H), 1.55-1.95 (m, 8H), 3.94 (sep, J=7.2 Hz, 2H), 4.08 (sep, J=7.2 Hz, 2H). ³¹P NMR (121 MHz, CD₂Cl₂) δ=−16.77 ppm. ¹³C NMR (100 MHz, CD₂Cl₂) δ=21.1, 21.2, 22.0 (bs), 26.5, 27.3, 27.4, 27.6, 27.7, 31.5, 31.6, 31.9, 32.1, 36.2 (d, J=13.7 Hz), 53.2 (bs), 107.1 (d, J=78.8 Hz), 142.2 ppm. IR (neat) ν=680, 1035, 1050, 1548, 1862, 2847, 2919 cm⁻¹. (ESI)MS calculated for $C_{27}H_{50}N_2P^+$: 433.4. found 433.5.

Compound 4

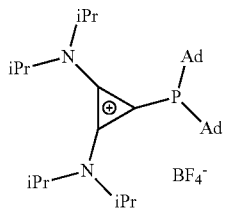

Diadamantylphosphine (1.26 g, 4.17 mmol) was added to a mixture of chlorocyclopropenium salt 1 (500 mg, 1.39 mmol) in THF (5 ml) and the mixture obtained was heated at 60° C. for 72 hours. After cooling to ambient temperature, the solvent was removed under vacuum and the residue was dissolved in DCM (20 ml), washed with a saturated NaBF₄ solution (3×15 ml) and dried over Na₂SO₄. The organic phase was evaporated and the residue was washed with Et₂O (3×10 ml and gave the desired compound as a white solid (680 mg, 79%).

¹H NMR (300 MHz, CD₂Cl₂) δ=1.30 (d, J=6.9 Hz, 6H), 1.38 (d, J=6.9 Hz, 12H), 1.45 (d, J=6.9 Hz, 6H), 1.56-1.77 (m, 12H), 1.84 (bs, 12H), 2.04 (bs, 6H), 3.76-3.83 (m, 1H), 3.92 (sep, J=7.2 Hz, 1H), 4.36 (sep, J=6.9 Hz, 1H), 4.57 (sep, J=6.9 Hz, 1H); ³¹P NMR (121 MHz, CD₂Cl₂) δ=15.63 ppm. ¹³C NMR (75 MHz, CD₂Cl₂) δ=20.9, 21.4, 21.5, 21.6, 23.3, 29.5 (d, J=8.5 Hz), 37.0, 39.5 (d, J=25.2 Hz), 42.9 (d, J=11.5 Hz), 49.9, 57.5, 57.6, 105.0 (d, J=90.5 Hz), 145.2 ppm (d, J=22.4 Hz). IR (neat) ν□=1033, 1048, 1089, 1375, 1452, 1539, 1851, 2848, 2901 cm⁻¹. HRMS calculated for $C_{35}H_{58}N_2P^+$: 537.433212. found 537.433029.

Compound 5

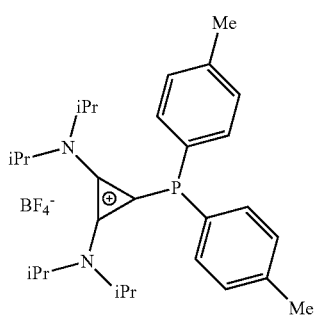

Di(p-tolyl)phosphine (1.80 g, 8.40 mmol) was added to a mixture of chlorocyclopropenium salt 1 (1.00 g, 2.80 mmol) in THF (20 ml) and the mixture obtained was heated at 60° C. for 24 hours. After cooling to ambient temperature, the solvent was removed under vacuum and the residue was dissolved in DCM (20 ml), washed with a saturated NaBF₄ solution (3×15 ml) and dried over Na₂SO₄. The organic phase was evaporated and the residue was washed with Et₂O (3×20 ml); the desired compound was obtained as a white solid (1.44 g, 96%).

¹H NMR (400 MHz, CD₂Cl₂) δ=0.97 (d, J=6.6 Hz, 12H), 1.27 (d, J=6.8 Hz, 12H), 2.31 (s, 6H), 3.32 (sep, J=6.6 Hz, 2H), 3.98 (sep, J=6.8 Hz, 2H), 7.20-7.21 ppm (m, 8H). ³¹P NMR (161 MHz, CD₂Cl₂) δ=−24.12 ppm. ¹³C NMR (121 MHz, CD₂Cl₂) δ=21.5, 21.6, 21.9, 22.0 (bs), 53.4 (bs), 108.1 (d, J=67.8 Hz), 127.9 (d, J=6.1 Hz), 131.2 (d, J=8.1 Hz), 134.6 (d, J=22.3 Hz), 139.4, 142.4 ppm. IR (neat) ν=686, 811, 1048, 1547, 1863, 2976 cm⁻¹. HRMS calculated for $C_{29}H_{42}N_2P^+$: 449.308012. found 449.308455.

Compound 6

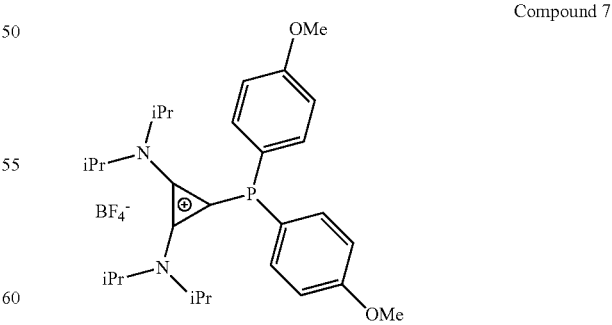

Di(p-fluorophenyl)phosphine (2.67 g, 12.0 mmol) was added to a mixture of chlorocyclopropenium salt 1 (1.44 g, 4.00 mmol) in THF (20 ml) and the mixture obtained was heated at 60° C. for 24 hours. After cooling to ambient temperature, the solvent was removed under vacuum and the residue was dissolved in DCM (20 ml), washed with a saturated NaBF₄ solution (3×15 ml) and dried over Na₂SO₄. The organic phase was evaporated and the residue was washed with Et₂O (3×20 ml); the desired compound was obtained as a white solid (1.65 g, 76%).

¹H NMR (400 MHz, CD₂Cl₂) δ=0.99 (d, J=6.8 Hz, 12H), 1.29 (d, J=6.9 Hz, 12H), 3.35 (sep, J=6.8 Hz, 2H), 4.00 (sep, J=6.9 Hz, 2H), 7.15 (m, 4H), 7.41 ppm (m, 4H). ³¹P NMR (161 MHz, CD₂Cl₂) δ=−24.57 ppm. ¹³C NMR (100 MHz, CD₂Cl₂) δ=21.5, 21.6, 21.9, 54.0 (bs), 108.8 (d, J=58.5 Hz), 117.8 (dd, J=21.2, 9.2 Hz), 127.0 (dd, J=7.1, 4.0 Hz), 137.1 (dd, J=23.2, 9.1 Hz), 139.6, 165.4 ppm (d, J=252.6 Hz). IR (neat) ν=691, 836, 1049, 1552, 1869, 2987 cm⁻¹. (ESI) MS calculated for $C_{27}H_{36}F_2N_2P^+$ 457.26, found 457.29. HRMS calculated for $C_{27}H_{36}F_2N_2P^+$: 457.257868. found 457.257700.

Compound 7

Di(p-methoxyphenyl)phosphine (0.875 g, 3.6 mmol) was added to a mixture of chlorocyclopropenium salt 1 (430 mg, 1.2 mmol) in THF (5 ml) and the mixture obtained was heated at 60° C. for 12 hours. After cooling to ambient temperature, the solvent was removed under vacuum and the residue was dissolved in DCM (20 ml), washed with saturated NaBF$_4$ solution (3×15 ml) and dried over Na$_2$SO$_4$. The organic phase was evaporated and the residue was purified via silica gel flash chromatography (DCM:acetone=9:1); the desired compound was obtained as a white solid (0.55 g, 80%).

$^1$H-NMR (300 MHz, CD$_2$Cl$_2$) δ=0.97 (d, J=6.8 Hz, 12H), 1.27 (d, J=6.9 Hz, 12H), 3.34 (sep, J=6.8 Hz, 2H), 3.76 (s, 6H), 3.97 (sep, J=6.9 Hz, 2H), 6.94 (m, 4H), 7.31 ppm (m, 4H). $^{31}$P NMR (300 MHz, CD$_2$Cl$_2$) δ=−23.83 ppm. $^{13}$C NMR (75 MHz, CD$_2$Cl$_2$) δ=21.6, 21.7, 22.0, 56.3, 108.1 (d, J=67.4 Hz), 116.0 (d, J=9.1 Hz), 122.0 (d, J=3.3 Hz), 136.6 (d, J=23.4 Hz), 139.2 (d, J=1.3 Hz), 162.8 ppm. IR (neat) ν=684, 834, 1024, 1247, 1553, 1866, 2982 cm$^{-1}$; (ESI) MS calculated for C$_{29}$H$_{42}$N$_2$O$_2$P$^+$: 481.30 found 481.37. HRMS calculated for C$_{29}$H$_{42}$N$_2$O$_2$P$^+$: 481.297843. found 481.297370.

(65 mg, 0.12 mmol) cooled to −20° C. The reaction mixture was allowed to heat up to ambient temperature and it was then stirred for a further 30 minutes. After the removal of the solvent residue under vacuum, the solid residue was washed with pentane (3×1 ml) and dried; the desired compound was obtained as a yellow solid (74 mg, 99%).

$^1$H NMR (300 MHz, CD$_2$Cl$_2$) δ=1.02 (d, J=7.0 Hz, 24H), 1.36 (d, J=7.0 Hz, 24H), 3.45 (sep, J=7.0 Hz, 4H), 4.13 (sep, J=7.0 Hz, 4H), 7.34 (m, 8H), 8.28 ppm (m, 8H). $^{31}$P NMR (300 MHz, CD$_2$Cl$_2$) δ=26.12 ppm (d, J=131.3 Hz). $^{13}$C NMR (75 MHz, CD$_2$Cl$_2$) δ=21.3, 21.6, 54.0, 100.6 (t, J=15.1 Hz), 117.5 (dd, J=21.5, 6.3 Hz), 124.4 (t, J=4.7 Hz), 138.8 (dt, J=9.7, 8.5 Hz), 139.3 (dd, J=7.0, 3.7 Hz), 166.0 ppm (d, J=256.0 Hz). IR (neat) ν=687, 814, 1035, 1239, 1556, 1865, 1976, 2972 cm$^{-1}$. HRMS calculated for C$_{55}$H$_{72}$B$_3$ClF$_{16}$N$_4$OP$_2$Rh$^{-1}$: 1341.399085. found 1341.398831.

Compound 8

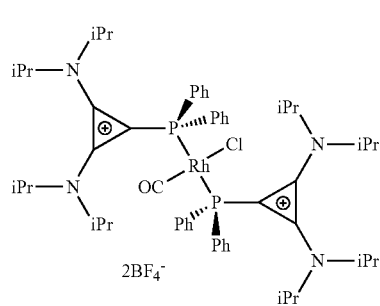

Dry THF (2 ml) was added to a solid mixture of [RhCl(CO)$_2$]$_2$ (10 mg, 0.025 mmol) and phosphenium salt 2 (50 mg, 0.1 mmol) cooled to −20° C. The reaction mixture was allowed to heat up to ambient temperature and to subsequently stir for a further 30 minutes. After the removal of the solvent under vacuum, the solid residue was washed with pentane (3×1 ml) and dried; the desired product was obtained as a yellow solid (56 mg, 93%).

$^1$H NMR (400 MHz, CD$_2$Cl$_2$) δ=0.89 (d, J=6.9 Hz, 24H), 1.27 (d, J=6.9 Hz, 24H), 3.39 (m, 4H), 4.04 (m, 4H), 7.52-7.62 (m, 10H), 8.08-8.16 ppm (m, 10H). $^{31}$P NMR (161 MHz, CD$_2$Cl$_2$) δ=30.15 ppm (d, J=133.1 Hz). $^{13}$C NMR (100 MHz, CD$_2$Cl$_2$) δ=21.2, 21.6, 55.0 (bs), 101.4 (t, J=13.4 Hz), 128.5 (t, J=25.8 Hz), 130.1 (t, J=5.8 Hz), 133.5, 134.3 (d, J=21.6 Hz), 136.1 (t, J=7.8 Hz), 139.2 ppm (t, J=4.3 Hz). IR (neat) ν=700, 800, 1036, 1053, 1552, 1865, 1970, 2975 cm$^{-1}$. HRMS calculated for C$_{53}$H$_{76}$BClF$_4$N$_4$OP$_2$Rh$^+$: 1095.427971; found 1095.427645.

Compound 10

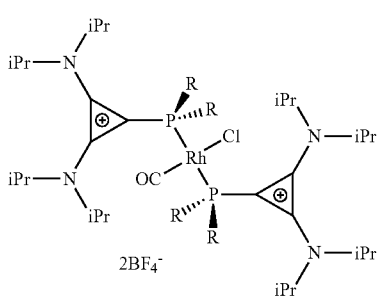

R = p-(OMe)C$_6$H$_4$

Dry THF (2 ml) was added to a solid mixture of [RhCl(CO)$_2$]$_2$ (9.0 mg, 0.023 mmol) and phosphenium salt 7 (52 mg, 0.091 mmol) cooled to −20° C. The reaction mixture was allowed to heat up to ambient temperature and was stirred for an additional 30 minutes. After the removal of the solvent under vacuum, the solid residue was washed with pentane (3×1 ml) and the desired compound was obtained as a yellow solid (61 mg, 99%).

$^1$H NMR (300 MHz, CD$_2$Cl$_2$) δ=0.91 (d, J=6.9 Hz, 24H), 1.25 (d, J=6.9 Hz, 24H), 3.42 (sep, J=6.9 Hz, 4H), 3.81 (s, 12H), 4.02 (sep, J=6.9 Hz, 4H), 7.04 (m, 8H), 8.02 ppm (m, 8H). $^{31}$P NMR (300 MHz, CD$_2$Cl$_2$) δ=27.12 ppm (d, J=130.3 Hz). $^{13}$C NMR (100 MHz, CD$_2$Cl$_2$) δ=21.5, 21.9, 24.0, 56.6, 103.2 (t, J=13.0 Hz), 115.8 (t, J=6.7 Hz), 119.8 (t, J=29.0 Hz), 138.3 (t, J=8.5 Hz), 139.3, (t, J=4.5 Hz), 164.2 ppm. IR (neat) ν=685, 800, 1053, 1257, 1551, 1864, 1977, 2979 cm$^{-1}$. HRMS calculated for C$_{59}$H$_{84}$B$_3$ClF$_{12}$N$_4$O$_5$P$_2$Rh$^-$: 1389.479175; found: 1389.478116.

Compound 9

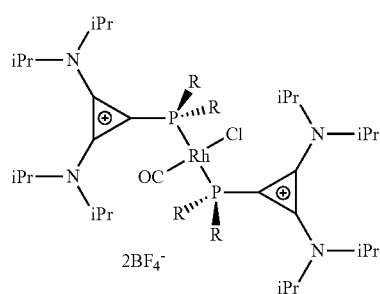

R = p-(F)C$_6$H$_4$

Dry THF (2 ml) was added to a solid mixture of [RhCl(CO)$_2$]$_2$ (12 mg, 0.030 mmol) and phosphenium salt 6

Compound 11

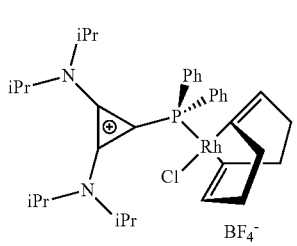

[RhCl(cod)]$_2$ (24.6 mg, 0.05 mmol) was added to a solution of 2 (50.9 mg, 0.10 mmol) in CH$_2$Cl$_2$ (2 ml) and the mixture obtained was stirred at ambient temperature for one hour.

Subsequently, the solvent was removed under vacuum and the yellow residue obtained was washed with pentane (2 ml) and dried; 11 was obtained as a yellow solid (72.4 mg, 96%).

$^1$H NMR (400 MHz, CD$_2$Cl$_2$) δ=1.09 (d, J=6.4 Hz, 12H), 1.33 (d, J=6.8 Hz, 12H), 1.98 (m, 2H), 2.08 (m, 2H), 2.29 (m, 4H), 3.54 (bs, 2H), 3.94 (bm, 2H), 4.10 (bm, 2H), 5.58 (bs, 2H), 7.39-7.70 (m, 10H); $^{13}$C NMR (100 MHz, CD$_2$Cl$_2$): 21.9, 22.4, 29.5 (bs), 33.7 (d, J=2.0 Hz), 53.3 (bs), 59.1 (bs), 72.9 (d, J=12.9 Hz), 102.9 (d, J=12.9 Hz), 108.6 (dd, J=7.0, 12.6 Hz), 128.0 (d, J=43.9 Hz), 130.3 (d, J=10.7 Hz), 133.3 (d, J=1.9 Hz), 135.1 (d, J=12.0 Hz), 139.2 (d, J=7.9 Hz); $^{31}$P NMR (100 MHz, CD$_2$Cl$_2$): 25.3 (d, J=150.6 Hz); IR (neat) ν=696, 752, 996, 1032, 1049, 1091, 1376, 1552, 1868, 2938, 2975 cm$^{-1}$; HRMS calculated for C$_{35}$H$_{50}$ClN$_2$PRh: 667.244969. found 667.245253.

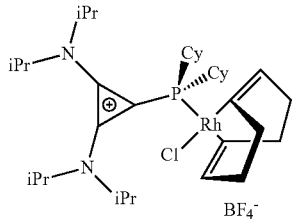

Compound 12

[RhCl(cod)]$_2$, (24.6 mg, 0.05 mmol) was added to a mixture of 3 (52.0 mg, 0.10 mmol) in CH$_2$Cl$_2$ (2 ml) and the mixture obtained was stirred at ambient temperature for one hour. Subsequently, the solvent was removed under vacuum and the yellow residue obtained was washed with pentane (2 ml) and dried; 12 was obtained as a yellow solid (67.4 mg, 88%).

$^1$H NMR (400 MHz, CD$_2$Cl$_2$) δ=1.23-1.45 (m, 8H), 1.50 (bs, 12H), 1.57 bs, 12H), 1.84 (bs, 4H), 1.96 (bs, 8H), 2.11-2.27 (m, 4H), 2.31-2.42 (m, 2H), 2.42-2.57 (m, 2H), 3.78 (bs, 2H), 4.22 (bs, 2H), 4.83 (bs, 2H), 5.51 (bs, 2H); $^{13}$C NMR (100 MHz, CD$_2$Cl$_2$): 22.2 (bs), 23.0 (bs), 26.2 (d, J=1.3 Hz), 27.2, 27.3, 27.4, 27.5, 28.8 (d, J=1.2 Hz), 30.5 (bs), 31.3, 31.6 (d, J=2.6 Hz), 33.6 (d, J=2.5 Hz), 34.6 (bs), 34.9 (bs), 58.8 (bs), 71.4 (d, J=13.0 Hz), 102.2, 107.8 (dd, J=12.0, 6.9 Hz), 141.4 (bs); $^{31}$P NMR (100 MHz, CD$_2$Cl$_2$): 28.3 (d, J=150.5 Hz); IR (neat) ν=727, 1004, 1050, 1093, 1535, 1860, 2852, 2933 cm$^{-1}$; HRMS calculated for C$_{35}$H$_{62}$ClN$_2$PRh: 679.338870. found: 679.338987.

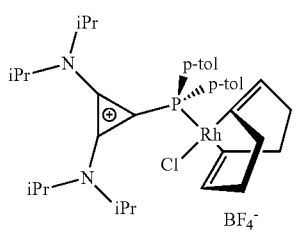

Compound 13

[RhCl(cod)]$_2$ (25.0 mg, 0.05 mmol) was added to a solution of 5 (54.0 mg, 0.10 mmol) in CH$_2$Cl$_2$ (2 ml) and the mixture obtained was stirred at ambient temperature for one hour. Subsequently, the solvent was removed under vacuum and the yellow solid obtained was washed with pentane (2 ml) and dried; 13 was obtained as a yellow solid (77.0 mg, 99%).

$^1$H NMR (400 MHz, CD$_2$Cl$_2$) δ=1.08 (d, J=6.5 Hz, 12H), 1.32 (d, J=6.7 Hz, 12H), 1.92-2.11 (m, 4H), 2.18-2.33 (m, 4H), 2.35 (s, 6H), 3.51 (m, 2H), 3.95 (m, 2H), 4.08 (m, 2H), 5.54 (m, 2H), 7.23-7.29 (m, 4H), 7.43-7.50 ppm (m, 4H). $^{31}$P NMR (121 MHz, CD$_2$Cl$_2$) δ=24.66 ppm (d, J=151.0 Hz). $^{13}$C NMR (100 MHz, CD$_2$Cl$_2$) δ=21.9, 22.0, 22.4, 29.5, 33.7 (d, J=2.9 Hz), 53.2 (bs), 56.0 (bs), 72.7 (d, J=12.9 Hz), 103.5 (d, J=15.7 Hz), 108.3 (dd, J=12.7, 6.9 Hz), 124.5 (d, J=46.0 Hz), 130.9 (d, J=10.1 Hz), 135.0 (d, J=12.2 Hz), 139.1 (d, J=8.4 Hz), 142.2 ppm (d, J=2.0 Hz). IR (neat) ν=677, 808, 1053, 1552, 1863, 2969 cm$^{-1}$. HRMS calculated for C$_{37}$H$_{54}$ClN$_2$PRh$^+$: 695.276269. found 695.276236.

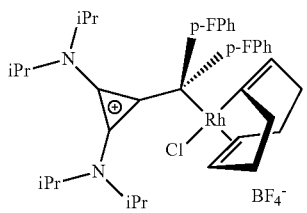

Compound 14

[RhCl(cod)]$_2$ (25.0 mg, 0.05 mmol) was added to a solution of 6 (54.0 mg, 0.10 mmol) in CH$_2$Cl$_2$ (2 ml) and the mixture obtained was stirred at ambient temperature for one hour. Subsequently, the solvent was removed under vacuum and the yellow residue obtained was washed with pentane (2 ml) and dried; 14 was obtained as a yellow solid (77.0 mg, 97%).

$^1$H NMR (300 MHz, CD$_2$Cl$_2$) δ=1.22 (d, J=6.7 Hz, 12H), 1.45 (d, J=6.5 Hz, 12H), 2.05-2.28 (m, 4H), 2.30-2.56 (m, 4H), 3.65 (m, 2H), 4.03 (m, 2H), 4.21 (m, 2H), 5.70 (m, 2H), 7.26-7.37 (m, 4H), 7.73-7.86 ppm (m, 4H). $^{31}$P NMR (121 MHz, CD$_2$Cl$_2$) δ=22.65 ppm (d, J=153.0 Hz). $^{13}$C NMR (100 MHz, CD$_2$Cl$_2$) δ=21.6, 21.9, 29.1 (bs), 33.3 (d, J=2.4 Hz), 55.5 (bs), 57.6, 72.4 (d, J=13.0 Hz), 101.6 (d, J=19.3 Hz), 108.5 (dd, J=12.4, 7.2 Hz), 117.3 (dd, J=21.5, 11.5 Hz), 123.5 (dd, J=45.9, 2.5 Hz), 137.4 (dd, J=14.8, 8.9 Hz), 138.9 (dd, J=7.2, 1.4 Hz), 165.6 ppm (dd, J=256.0 Hz, J=2.4 Hz). IR (neat) ν=681, 815, 1053, 1548, 1865, 2976 cm$^{-1}$. HRMS calculated for C$_{35}$H$_{48}$ClF$_2$N$_2$PRh$^+$: 703.226126. found 703.225916.

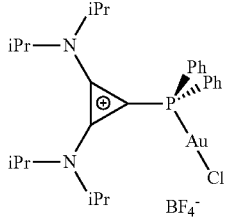

Compound 15

[AuCl(Me$_2$S)] (63.0 mg, 0.20 mmol) was added to a suspension of salt 2 (109.0 mg, 0.20 mmol) in dry THF (3 ml) cooled to −20° C. and stirred at this temperature for one hour. The solvent was removed under vacuum at 0° C. and the desired product was obtained as an off-white solid (154 mg, 97%).

$^1$H NMR (400 MHz, CD$_2$Cl$_2$) δ=0.96 (d, J=6.9 Hz, 12H), 1.33 (d, J=6.9 Hz, 12H), 3.35 (sep, J=6.9 Hz, 2H), 4.07 (sep, J=6.9 Hz, 2H), 7.54-7.64 (m, 6H), 7.86-7.93 ppm (m, 4H). $^{31}$P NMR (161 MHz, CD$_2$Cl$_2$) δ=17.86 ppm. $^{13}$C NMR (300 MHz, CD$_2$Cl$_2$) δ=21.9, 22.0, 68.5, 96.8 (d, J=45.3 Hz), 125.5

(d, J=67.5 Hz), 131.1 (d, J=13.6 Hz), 134.7 (d, J=2.6 Hz), 135.9 (d, J=16.2 Hz), 138.7 ppm. IR (neat) ν=692, 751, 1057, 1568, 1866, 2979 cm$^{-1}$. HRMS calculated for $C_{27}H_{38}AuClN_2P^+$: 653.212121. found 653.213006.

Compound 16

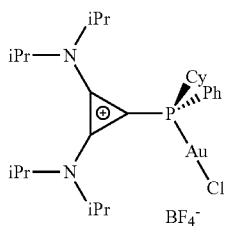

[AuCl(Me$_2$S)] (29.5 mg, 0.10 mmol) was added to a suspension of salt 3 (52.0 mg, 0.10 mmol) in dry CH$_2$Cl$_2$ (3 ml) cooled to −20° C. and were stirred at this temperature for one hour. The solvent was removed under vacuum at 0° C. and the desired product was obtained as an off-white solid (70.8 mg, 94%).

$^1$H NMR (300 MHz, CD$_2$Cl$_2$) δ=1.23-1.45 (m, 10H), 1.51 (d, J=5.7 Hz, 12H), 1.63 (d, J=6.9 Hz, 12H), 1.65-1.82 (m, 4H), 1.94 (bs, 4H), 2.10-2.16 (m, 2H), 2.36-2.50 (m, 2H), 4.16 (sep, J=6.9 Hz, 2H), 4.27 ppm (sep, J=6.9 Hz, 2H). $^{31}$P NMR (121 MHz, CD$_2$Cl$_2$) δ=33.31 ppm. $^{13}$C NMR (75 MHz, CD$_2$Cl$_2$) δ=22.0, 22.1, 25.8 (bs), 26.8 (d, J=15.5 Hz), 27.1 (d, J=13.4 Hz), 30.8, 30.9, 32.1, 32.2, 38.0 (d, J=32.1 Hz), 54.5 (bs), 68.5, 95.1 (bs), 141.1 ppm. IR (neat) ν=682, 1029, 1051, 1558, 1863, 2851, 2928 cm$^{-1}$. HRMS calculated for $C_{27}H_{50}AuClN_2P^+$: 665.306018. found 665.306796.

Compound 17

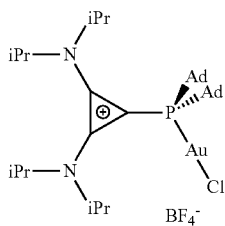

[AuCl(Me$_2$S)] (29.5 mg, 0.10 mmol) was added to a suspension of the salt 4 (62.5 mg, 0.10 mmol) in dry CH$_2$Cl$_2$ (3 ml)) cooled to −20° C. and was stirred at this temperature for one hour. The solvent was then removed under vacuum at 0° C. and the desired product was obtained as an off-white solid (81.4 mg, 95%).

$^1$H NMR (400 MHz, CD$_2$Cl$_2$) δ=1.28 (d, J=6.4 Hz, 8H), 1.39 (d, J=6.8 Hz, 12H), 1.62 (bs, 6H), 1.71 (s, 10H), 2.00-2.14 (m, 18H), 4.12 (bs, 1H), 4.36 (bs, 1H), 4.43 ppm (sep, J=6.8 Hz, 2H). $^{31}$P NMR (161 MHz, CD$_2$Cl$_2$) δ=33.31 ppm (bs). $^{13}$C NMR (100 MHz, CD$_2$Cl$_2$) δ=21.7 (bs), 22.7 (bs), 23.0, 28.9, 29.1, 36.0, 36.1, 42.3, 42.4, 44.7 (bs), 54.0, 54.2, 54.3, 58.2, 93.7 (bs), the two C—N from the cyclopropenium cations were not detected after extended measurement. IR (neat) ν=672, 734, 1055, 1551, 1842, 2899 cm$^{-1}$. HRMS calculated for $C_{35}H_{58}AuClN_2P^+$: 769.368616. found 769.368204.

Compound 18

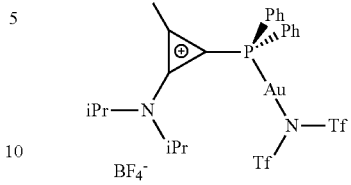

AgNTf$_2$ (77.6 mg, 0.20 mmol) was added to a suspension of the complex 15 (148.2 mg, 0.20 mmol) in dry CH$_2$Cl$_2$ (3 ml) cooled to 0° C. and was stirred at this temperature for one hour. The reaction mixture was filtered through a Celite plug. After removing the solvent under vacuum, the desired product was obtained as an offwhite solid (169 mg, 96%).

$^1$H NMR (400 MHz, CD$_2$Cl$_2$) δ=0.95 (d, J=7.2 Hz, 12H), 1.32 (d, J=7.2 Hz, 12H), 3.27 (sep, J=6.8 Hz, 2H), 4.08 (sep, J=6.8 Hz, 2H), 7.52-7.66 (m, 6H), 7.81-7.95 ppm (m, 4H). 31P NMR (161 MHz, CD$_2$Cl$_2$) δ=14.47 ppm. $^{13}$C NMR (400 MHz, CD$_2$Cl$_2$) δ=21.9, 22.0, 55.4 (bs), 94.6 (d, J=54.8 Hz), 120.2 (q, J=320.2 Hz), 124.3 (d, J=71.6 Hz), 131.4 (d, J=13.5 Hz), 135.2 (d, J=2.5 Hz), 135.9 (d, 16.8 Hz), 139.0 ppm (d, J=7.6 Hz). IR (neat) ν=691, 956, 1052, 1130, 1182, 1351, 1401, 1439, 1567, 1866, 2986 cm$^{-1}$. HRMS calculated for $C_{29}H_{38}AuClN_3O_4F_6PS_2^+$: 898.160568. found 898.160583.

Compound 19

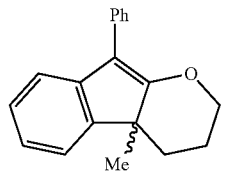

(1.0 mg, 0.001 mmol) of the catalyst 17 were added, with stirring, to a solution of the alcohol 20 (see page 7) (0.1 mmol) in dry DCM (2 ml) and the reaction mixture was stirred at ambient temperature for 30 minutes. The reaction mixture was filtered via a silica plug. After removing the solvent under vacuum, the target compound was obtained (27 mg, 97% yield).

$^1$H NMR (300 MHz, CD$_2$Cl$_2$) δ=1.30 (s, 3H), 1.45-16.1 (m, 2H), 2.13-2.31 (m, 2H), 3.54-3.64 (m, 1H), 4.28-4.36 (m, 1H), 7.06 (dt, J=7.3, 1.3 Hz, 1H), 7.14 (dt, J=7.4, 1.4 Hz, 1H), 7.18-7.26 (m, 2H), 7.31-7.38 (m, 3H), 7.47-7.52 ppm (m, 2H). $^{13}$C NMR (300 MHz, CD$_2$Cl$_2$) δ=22.9, 23.0, 33.8, 45.2, 73.3, 118.2, 120.3, 121.8, 124.6, 127.3, 127.5, 129.0, 129.4, 133.9, 142.3, 149.7, 166.2 ppm. IR (neat) ν=757, 1002, 1069, 1140, 1305, 1445, 1619, 2874, 2931 cm$^{-1}$. HRMS calculated for $C_{19}H_{18}O$: 262.135762. found: 262.135495.

Compound 20

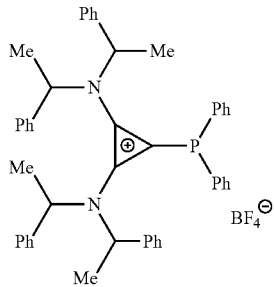

Diphenylphosphine (1.3 ml, 7.6 mmol) was added to a mixture of the corresponding chlorocyclopropenium salt (1.56 g, 2.5 mmol) in THF (10 ml) and the mixture obtained was heated at 60° C. for 24 hours. After cooling to ambient temperature, the solvent was removed under vacuum and the residue was dissolved in DCM (20 ml), washed with a saturated solution of NaBF$_4$ (3×25 ml) and dried over Na$_2$SO$_4$. The organic phase was evaporated and the residue was washed with Et$_2$O (3×10 ml). The compound was obtained as a white solid (0.96 g, 48%).

$^1$H NMR (300 MHz, CDCl$_3$) δ=1.44 (d, J=7.2 Hz, 6H), 1.83 (d, J=7.2 Hz, 6H), 4.26 (q, J=7.2 Hz, 2H), 4.62 (q, J=7.2 Hz, 2H), 6.48-6.57 (m, 4H), 6.72-6.81 (m, 4H), 6.95-7.09 (m, 12H), 7.22-7.39 (m, 8H), 7.41-7.49 ppm (m, 2H). $^{31}$P NMR (121 MHz, CDCl$_3$) δ=−22.31 ppm. $^{13}$C NMR (75 MHz, CDCl$_3$) δ=17.6, 18.0, 57.3 (br.s), 60.2 (br.s), 109.3 (d, J=69.4 Hz), 126.2 (d, J=27.2 Hz), 127.5, 127.7 (d, J=17.5 Hz), 128.3 (d, J=7.9 Hz), 128.6 (d, J=7.8 Hz), 129.5 (d, J=11.0 Hz), 130.7 (d, J=10.1 Hz), 132.7, 133.0, 133.2, 135.7, 136.4, 140.3 ppm (d, J=2.0 Hz). IR (neat) ν=694, 1050, 1524, 1858, 3054 cm$^{-1}$. HRMS calculated for C$_{47}$H$_{46}$N$_2$P$^+$: 669.339313. found 669.339366.

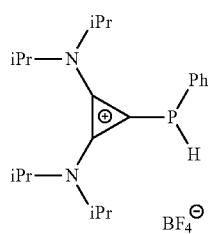

Compound 21

Phenylphosphine (7.4 ml, 5.3 mmol, 10% solution in hexane) was added to a mixture of chlorocyclopropenium salt 1 (630.0 mg, 1.8 mmol) in THF (6 ml) and the mixture obtained was heated at 60° C. for 24 hours. After cooling to ambient temperature, the solvent was removed under vacuum and the residue was dissolved in DCM (15 ml), washed with a saturated solution of NaBF$_4$ (3×25 ml) and dried over Na$_2$SO$_4$. The compound was obtained as a white solid (575 mg, 76%).

$^1$H NMR (300 MHz, CDCl$_3$) δ=1.12 (d, J=6.9 Hz, 6H), 1.31-1.46 (m, 18H), 3.64-3.80 (m, 2H), 4.14 (sept, J=6.9 Hz, 2H), 5.63 (d, J=233.6 Hz, 1H) 7.44-7.51 (m, 3H), 7.64-7.72 ppm (m, 2H). $^{31}$P NMR (161 MHz, CDCl$_3$) δ=−70.88 ppm. $^{13}$C NMR (100 MHz, CD$_2$Cl$_2$) δ=21.6, 21.8, 22.9, 50.8, 56.7, 105.5 (d, J=58.7 Hz), 126.0, 130.4 (d, J=8.1 Hz), 132.3, 137.1 (d, J=20.2 Hz), 138.7 ppm (d, J=4.1 Hz). IR (neat) ν=729, 1032, 1349, 1558, 1872, 2984 cm$^1$. HRMS calculated for C$_{21}$H$_{34}$N$_2$P$^+$: 345.245415. found 345.245568.

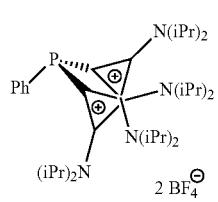

Compound 22

KHMDS (215.7 mg, 1.08 mmol) was added to a mixture of salt 21 (425.0 mg, 0.98 mmol) in THF (6 ml) and the mixture obtained was stirred at −40° C. for 2 hours. The solvent was removed under vacuum and the residue was dissolved in DCM (15 ml), washed with a saturated solution of NaBF$_4$ (3×15 ml) and dried over Na$_2$SO$_4$. The organic phase was evaporated and the residue was washed with THF (3×10 ml). The compound was obtained as a white solid (0.5156 g, 69%).

$^1$H NMR (400 MHz, CD$_2$Cl$_2$) δ=1.21 (d, J=6.9 Hz, 12H), 1.25 (d, J=6.9 Hz, 12H), 1.38 (d, J=6.9 Hz, 12H), 1.44 (d, J=6.9 Hz, 12H), 3.64 (sept, J=6.9 Hz, 4H), 4.17 (sept, J=6.9 Hz, 4H), 7.62-7.68 (m, 3H), 7.73-7.80 ppm (m, 2H). $^{31}$P NMR (161 MHz, CD$_2$Cl$_2$) δ=−48.31 ppm. $^{13}$C NMR (100 MHz, CD$_2$Cl$_2$) δ=21.2, 21.5, 21.5, 21.6, 21.6, 21.7, 53.4, 54.8, 98.2 (d, J=59.5 Hz), 125.0 (d, J=4.6 Hz), 131.1 (d, J=8.9 Hz), 133.0, 134.8 (d, J=22.9 Hz), 140.0 ppm. IR (neat) ν=694, 1029, 1151, 1357, 1555, 1858, 2974 cm$^{-1}$. HRMS calculated for C$_{36}$H$_{61}$BF$_4$N$_4$P$^+$: 667.467509. found 667.467401.

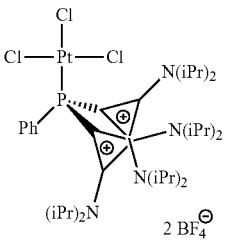

Compound 23

K$_2$PtCl$_4$ (44.8 mg, 0.117 mmol) was added to a mixture of salt 22 (88 mg, 0.117 mmol) in CH$_3$CN (2 ml) and the mixture obtained was stirred for 16 hours. After cooling to ambient temperature, the solvent was removed under vacuum, the residue was dissolved in DCM (5 ml) and filtered, and the solvent was allowed to evaporate. The compound was obtained as a yellow solid (111 mg, 98%).

$^1$H NMR (400 MHz, CD$_2$Cl$_2$) δ=1.10 (d, J=6.4 Hz, 12H), 1.14 (d, J=6.4 Hz, 12H), 1.33 (d, J=7.0 Hz, 12H), 1.36 (d, J=7.0 Hz, 12H), 4.05-4.18 (m, 4H), 4.29-4.43 (m, 4H), 7.58-7.67 (m, 3H), 8.37-8.46 ppm (m, 2H). $^{31}$P NMR (161 MHz, CD$_2$Cl$_2$) δ=−21.24 ppm (J=1994.8 Hz). $^{13}$C NMR (100 MHz, CD$_2$Cl$_2$) δ=17.5, 18.1, 18.5, 53.4, 90.6 (d, J=51.5 Hz), 118.9 (d, J=70.8 Hz), 126.8 (d, J=12.9 Hz), 130.9 (d, J=2.3 Hz), 133.5 (d, J=13.5 Hz), 134.7 ppm (d, J=8.6 Hz). IR (neat) ν=679, 1050, 1148, 1376, 1557, 1850, 2977 cm$^{-1}$. HRMS calculated for C$_{36}$H$_{61}$Cl$_3$N$_4$PPt$^+$: 880.333066. found 880.333903.

Using compound 23, 95% of 2-ethynyl-1,1'-binaphtyl were reacted in the presence of Ag(C$_2$B$_{10}$H$_5$Cl$_6$) to give [5]helicene.

The invention claimed is:
1. A phosphenium compound with the general formula I:

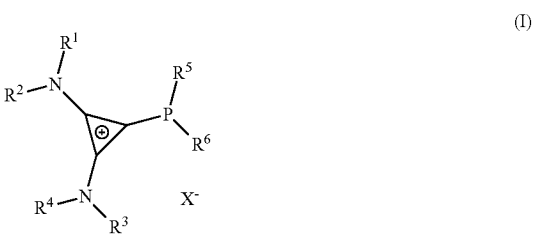

(I)

in which R$^1$, R$^2$, R$^3$ and R$^4$ are identical or different and represent a linear or branched C$_1$-C$_6$-alkyl radical, which can optionally be substituted, or $R^1$ and $R^2$ and/or $R^3$ and $R^4$ are bonded to one another with the formation of a ring, $R^5$ and $R^6$ stand for a saturated or unsaturated and linear or branched alkyl group, alkenyl group or aryl group, which can have suitable substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, and $X^-$ represents an anion chosen from $BF_4^-$, $PF_6^-$, $SbF_6^-$ and/or $BPh_4^-$.

2. The phosphenium compound as claimed in claim 1, wherein $R^1$, $R^2$, $R^3$ and $R^4$, each independently of one another, are chosen from isopropyl and tert-butyl.

3. A process for the preparation of the phosphenium compound with the general formula I as claimed in claim 1, said process comprising: reacting the halocyclopropenium salt with the general formula II:

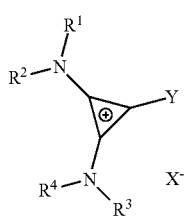

(II)

in which $R^1$, $R^2$, $R^3$ and $R^4$ are defined in claim 1 and Y represents a halogen atom, with a phosphine of the general formula III:

HPR⁵R⁶    III in which $R^5$ and $R^6$ are defined as in claim 1.

4. The process as claimed in claim 3, wherein Y represents chlorine.

5. A metal complex comprising as a ligand a phosphenium compound of the general formula I:

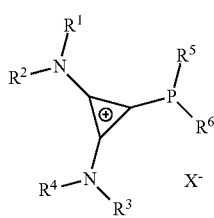

(I)

in which $R^1$, $R^2$, $R^3$ and $R^4$ are identical or different and represent a linear or branched $C_1$-$C_6$-alkyl radical, which can optionally be substituted, or $R^1$ and $R^2$ and/or $R^3$ and $R^4$ are bonded to one another with the formation of a ring, $R^5$ and $R^6$ stand for a saturated or unsaturated and linear or branched alkyl group, alkenyl group or aryl group, which can have suitable substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, and $X^-$ represents an anion.

6. A metal complex as claimed in claim 5, having the general formula IV:

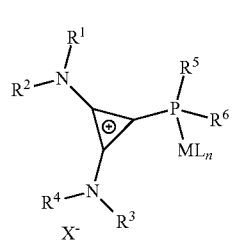

(IV)

in which $R^1$, $R^2$, $R^3$ and $R^4$ are identical or different and represent a linear or branched $C_1$-$C_6$-alkyl radical, which can optionally be substituted, or $R^1$ and $R^2$ and/or $R^3$ and $R^4$ are bonded to one another with the formation of a ring, $R^5$ and $R^6$ stand for a saturated or unsaturated and linear or branched alkyl group, alkenyl group or aryl group, which can have suitable substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, $X^-$ represents an anion, M represents a metal atom chosen from the group consisting of B, Cu, Ag, Au, Ru, Rh, Pd, Os, Ir and Pt, L represents n identical or different ligands and n represents a number from 1 to 3.

7. The metal complex as claimed in claim 6, wherein the ligands L are chosen from halogen, CN, CO, alkenes, cycloalkenes and/or alkynes.

8. The metal complex as claimed in claim 6, wherein $ML_n$ represents AuCl, $AuCl_3$, PdCl(allyl), RhCl(cod), $RhCl(CO)_2$, CuCl, $RhCl_4^-$ and/or $BH_3$.

9. A cycloisomerization reaction catalyzed by the metal complex as claimed in claim 6.

10. The phosphenium compound as claimed in claim 1, wherein:

$R^1$, $R^2$, $R^3$ and $R^4$, each independently of one another, are chosen from isopropyl and tert-butyl; and $R^5$ and $R^6$, each independently of one another, are chosen from linear, branched or cyclic alkyl, alkenyl, or aryl, each of which is unsubstituted or substituted.

11. A phosphenium compound with the general formula I:

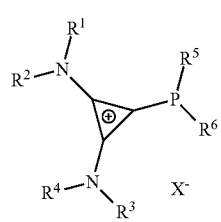

(I)

in which $R^1$, $R^2$, $R^3$ and $R^4$ are identical or different and are chosen from isopropyl and tert-butyl, $R^5$ and $R^6$ stand for a saturated or unsaturated and linear or branched alkyl group, alkenyl group or aryl group, which can have suitable substituents, or a heteroatom-comprising hydrocarbon group, which can have suitable substituents, and the $R^5$ and $R^6$ radicals can form a ring which can be 4- to 20-membered, saturated or unsaturated and alicyclic or heteroalicyclic and can exhibit suitable substituents, and $X^-$ represents an anion.

12. The phosphenium compound as claimed in claim 11, wherein $X^-$ is chosen from $BF_4^-$, $PF_6^-$, $SbF_6^-$ and/or $BPh_4^-$.

* * * * *